US006640122B2

(12) United States Patent  
Manoli et al.

(10) Patent No.: US 6,640,122 B2
(45) Date of Patent: Oct. 28, 2003

(54) EEG ELECTRODE AND EEG ELECTRODE LOCATOR ASSEMBLY

(75) Inventors: Samir Manoli, El Paso, TX (US); Daniel J. Levendowski, Carlsbad, CA (US); Eugene F. Davis, San Diego, CA (US); Christine Berka, Carlsbad, CA (US)

(73) Assignee: Advanced Brain Monitoring, Inc., Carlsbad, CA (US)

(*) Notice: Subject to any disclaimer, the term of this patent is extended or adjusted under 35 U.S.C. 154(b) by 1 day.

(21) Appl. No.: 09/900,988

(22) Filed: Jul. 9, 2001

(65) Prior Publication Data

US 2001/0044573 A1 Nov. 22, 2001

Related U.S. Application Data

(63) Continuation-in-part of application No. 09/492,380, filed on Jan. 27, 2000, now Pat. No. 6,381,481, which is a continuation-in-part of application No. 09/245,784, filed on Feb. 5, 1999, now Pat. No. 6,161,030.

(51) Int. Cl.[7] .............................................. A61B 5/0478
(52) U.S. Cl. ...................... 600/383; 600/393; 600/397; 607/139; 607/153
(58) Field of Search ................................ 600/383, 390, 600/393, 395–397, 544, 372; 607/139, 153

(56) References Cited

U.S. PATENT DOCUMENTS

| | | | | |
|---|---|---|---|---|
| 2,621,657 A | * | 12/1952 | Leech | 600/397 |
| 2,902,030 A | | 9/1959 | Kennedy et al. | 600/544 |
| 3,490,439 A | | 1/1970 | Rolston | |
| 3,507,541 A | * | 4/1970 | Westbrook et al. | 600/383 |
| 3,623,477 A | | 11/1971 | Trent | |
| 3,788,317 A | * | 1/1974 | McCormick | 600/397 |
| 3,877,466 A | | 4/1975 | Montor | 600/544 |
| 3,942,517 A | * | 3/1976 | Bowles et al. | 600/397 |
| 3,998,213 A | | 12/1976 | Price | |
| 4,033,334 A | * | 7/1977 | Fletcher et al. | 600/383 |
| 4,166,457 A | * | 9/1979 | Jacobsen et al. | 600/397 |
| 4,537,198 A | | 8/1985 | Corbett | |
| 4,632,120 A | | 12/1986 | Sherwin et al. | 128/639 |
| 4,709,702 A | | 12/1987 | Sherwin | |
| 4,770,180 A | | 9/1988 | Schmidt et al. | |
| 4,836,219 A | | 6/1989 | Hobson et al. | |

(List continued on next page.)

FOREIGN PATENT DOCUMENTS

WO        WO 00/45701 A1     2/2000

OTHER PUBLICATIONS

Article entitled "A Dry Electrode For EEG Recording," B. Taheri, R. Knight, and R. Smith, 1994 Elsevier Science Ireland Ltd. pp. 2–9.

*Primary Examiner*—Lee Cohen
(74) *Attorney, Agent, or Firm*—Fulwider Patton Lee & Utecht, LLP

(57) ABSTRACT

The EEG electrode and EEG electrode locator assembly may be used in combination with an EEG electrode locator headgear including a plurality of locator straps connectable to one or more of the EEG electrode locators that form an electrode locator assembly with the EEG electrode, for accurately positioning one or more of the EEG electrodes relative to the user's scalp, and for biasing the plurality of electrodes toward the user's scalp. The EEG electrode is adapted to be received in and cooperate with an EEG electrode locator ring, to form the electrode locator assembly. The EEG electrode includes a dispenser assembly adapted to dispense an electrically conductive gel onto the user's scalp to prepare the user's scalp. The dispenser assembly includes a base member and a porous foam pad lower cover to provide padding for a comfortable scalp interface, absorbs the conductive gel to maintain a consistent volume of gel between the electrode base and scalp, and for conducting EEG signals from the scalp of the user to a corresponding electrode locator ring for communication to an EEG monitor.

31 Claims, 6 Drawing Sheets

U.S. PATENT DOCUMENTS

| | | |
|---|---|---|
| 4,967,038 A | 10/1990 | Gevins et al. |
| 5,038,782 A | 8/1991 | Gevins et al. |
| 5,273,037 A | 12/1993 | Itil et al. |
| 5,291,888 A | 3/1994 | Tucker |
| 5,293,867 A | 3/1994 | Oommen |
| 5,348,006 A | 9/1994 | Tucker |
| 5,357,957 A | 10/1994 | Itil et al. |
| 5,404,875 A | 4/1995 | Gevins et al. |
| 5,479,934 A | 1/1996 | Imran |
| 5,564,433 A | 10/1996 | Thornton |
| 5,740,812 A | 4/1998 | Cowan ............. 600/544 |
| 5,800,351 A | 9/1998 | Mann |
| 5,813,993 A | 9/1998 | Kaplan et al. ............. 600/544 |
| 6,067,464 A | 5/2000 | Musha ............. 600/383 |
| 6,161,030 A * | 12/2000 | Levendowski et al. ..... 600/383 |
| 6,167,298 A | 12/2000 | Levin ............. 600/545 |
| 6,175,753 B1 | 1/2001 | Menkes et al. ............. 600/386 |
| 6,201,982 B1 | 3/2001 | Menkes et al. ............. 600/386 |
| 6,301,493 B1 * | 10/2001 | Marro et al. ............. 600/383 |
| 6,381,481 B1 * | 4/2002 | Levendowski et al. ..... 600/383 |
| 2001/0031930 A1 | 10/2001 | Roizen et al. ............. 600/544 |

* cited by examiner

EEG ELECTRODE AND EEG ELECTRODE LOCATOR ASSEMBLY

RELATED APPLICATIONS

This is a continuation in part of Ser. No. 09/492,380 filed Jan. 27, 2000, now U.S. Pat No. 6,381,481, which is a continuation in part of Ser. No. 09/245,784 filed Feb. 5, 1999, now U.S. Pat. No. 6,161,030.

GOVERNMENT LICENSE RIGHTS

The United States Government has rights in this invention pursuant to research supported in the whole or in part by NIH R44-NS38036 awarded by the National Institute of Neurological Disorders and Stroke.

BACKGROUND OF THE INVENTION

1. Field of the Invention

This invention relates generally to devices for the acquisition of electroencephalographic (EEG) signals, and more particularly concerns an EEG electrode and an EEG electrode locator assembly that can be applied by a user in combination with an EEG electrode locator headgear without assistance, for acquiring high quality EEG signals.

2. Description of Related Art

Advances in detection and characterization of electroencephalographic (EEG) signals from the brain have allowed EEG monitoring to be useful in analysis of neurological and sleep disorders, and laboratory studies of vigilance. Recent advances have, for example, provided much information about the correlation between EEG signals and an individual's level of arousal, in a continuum from vigilance to drowsiness, and sleep onset. Shifts in EEG signals have been directly correlated with changes in performance, particularly during tasks which require sustained attention over prolonged periods of time. Devices for monitoring EEG signals are typically used in a laboratory environment or in a home for sleep studies, but are typically set up and operated by trained technicians. However, application of EEG monitoring to environments for study and monitoring of brain performance, such as for monitoring brain activity in the home, office, aircraft cockpit, and train or truck operations cabins, for example, has been severely hampered by cumbersome detection and recording equipment, and the need for the assistance of a technician typically required to obtain high quality data.

In fitting EEG electrodes to the scalp of a subject being monitored, an EEG technician will typically first measure the distances between the nasium and the occipital bone, and between the mastoid processes, to identify the top center (Cz) of the head, and will then position all other electrodes relative to these landmarks to comply with the International 10/20 System that is well known in the art as the standard for positioning of EEG electrodes. The technician will then part the hair of the scalp of the subject at the intended electrode sites, clean the electrode sites to remove dirt, hair oil, and the like, and prepare the scalp to remove the top layer of dead skin, to ensure that scalp-electrode impedance values of less than 5 k$\Omega$ are obtained. The minimum level of impedance needed to minimize EEG artifact is dependent, in part, on the quality of the EEG amplifiers. Filtering certain environmental noises, such as 60 Hz interference, allows acceptable EEG signals to be acquired with impedance levels up to 100 k$\Omega$. Other artifacts are magnified as the impedances increase unless the signal acquisition equipment has been designed to minimize these effects. For example, replacing a conventional EEG system which uses wires to transmit non-amplified EEG to the data acquisition/storage unit with a system that amplifies and digitizes the signals on the head will help to reduce movement artifacts. Maintaining sufficient downward pressure on an electrode with higher impedance values will minimize the contribution of artifacts resulting from the electrode sliding across hair or the scalp.

Conventionally, after preparation of the intended electrode sites on the scalp, electrodes are glued to the scalp with collodion, typically a viscous solution of pyroxilin, a commercially available nitrocellulose, in ether and alcohol, that is a particularly noxious preparation that can bond with the scalp and hair, to provide a stable scalp-electrode interface, until dissolved by a solvent such as acetone, or a non-acetone, oil based collodion remover.

A variety of hats, caps, helmets and headgear are known that have been developed to position EEG electrodes according to the International 10/20 System and provide a scalp-electrode interface without the use of an adhesive such as collodion. However, these types of devices still require technician assistance in the preparation of the electrode site, and are commonly uncomfortable and unacceptable for use during activities of work and daily living. One such sleep monitoring headgear utilizes a circumferential elastic headband to generate an electrode seating pressure for a single electrode located at the top center of the head of a subject. It has been found, however, that when such a circumferential elastic headband is utilized to seat multiple electrodes, the headband slides up and posteriorly on the forehead.

Such conventional hats, caps, helmets and headgear also typically make it difficult for a user to part the hair or abrade their scalp at the electrode site without assistance. For example, most of the electrode caps require a technician to abrade the scalp with a blunt tipped syringe and then inject conductive gel into the electrode embedded into the cap. Another conventional device requires the technician to lift or turn a disposable electrode on its side after a conductive gel on the electrode has made contact with the hair of the scalp, in order to part the hair at the intended area of the scalp for placement of the electrode. Several systems intended for use in the laboratory for non-ambulatory EEG monitoring dispense electrode gel to the electrode, but would make an EEG electrode locator headgear uncomfortably heavy and inconvenient for ambulatory use outside a laboratory environment. Another type of device utilizes sharp tipped metal points to penetrate the dead layer of skin. However, such sharp metal points can pose a medical danger due to the potential for infection, particularly with repeated abrasions, and the possibility of penetration of the skull if the device were to be struck accidentally during ambulatory activity, or other activities during daily living.

It would therefore be desirable to provide an EEG electrode and an EEG electrode locator assembly for use in combination with an EEG electrode locator headgear that allows the user to apply the electrodes at the electrode sites, permitting conventional scalp preparation techniques to be applied by the user without technical assistance. The present invention meets these needs.

SUMMARY OF THE INVENTION

Briefly, and in general terms, the present invention provides for an EEG electrode and an EEG electrode assembly for use in combination with an EEG electrode locator headgear for a user that allows the user to locate and apply the EEG electrodes accurately according to the International 10/20 System without technical assistance, to allow the acquisition of high quality EEG signals. The EEG electrode locator headgear is of the type that is portable and comfortable, allowing it to be worn by the user during daily activities as one would a cap or visor. The EEG locator headgear typically includes a plurality of locator straps connectable to one or more of the EEG electrode locators that form an electrode locator assembly with the EEG electrode for accurately positioning one or more of the EEG electrodes relative to the user's scalp, and for biasing the plurality of electrodes toward the user's scalp. Each EEG electrode is adapted to be received in and cooperate with a corresponding EEG electrode locator ring. Each EEG electrode includes a dispenser assembly adapted to dispense an electrically conductive gel through the user's hair onto the user's scalp. The dispenser assembly includes a base member for conducting EEG signals from the scalp of the user to a corresponding electrode locator ring for signal transmission to an EEG monitor.

The invention accordingly provides for an electroencephalograph (EEG) electrode locator assembly for use in combination with an EEG electrode locator headgear for accurate positioning of the EEG electrode locator assembly on the scalp of a user. In a presently preferred embodiment, the EEG electrode assembly comprises an EEG electrode locator member adapted to be mounted to EEG electrode locator headgear; and an EEG electrode received in and removably electrically coupled to the EEG electrode locator headgear. The EEG electrode includes an electrically conductive base adapted to be in electrical communication with the scalp of a user for detecting EEG signals of the user. The EEG electrode and the electrically conductive base member typically may be made from a carbon and ABS composite plastic material with a silver/silver chloride (Ag/AgCl) coating. The EEG electrode locator member also typically may be made from a carbon and ABS composite plastic material with a Ag/AgCl coating, although the EEG electrode locator member may alternatively be made from another similar suitable electrically conductive material, such as stainless steel, for example. In one presently preferred aspect, the EEG electrode locator member comprises an electrically conductive ring having a central opening adapted to receive the EEG electrode. The EEG electrode locator member also preferably has a surface defining a plurality of slots for receiving and connection to one or more locator straps. The EEG electrode locator headgear preferably includes an electrical connector, and the EEG electrode locator member includes means for connecting the electrical connector to the EEG electrode locator member. In a presently preferred aspect, the means for connecting the electrical connector to the EEG electrode locator member comprises an electrical terminal connector aperture, and terminal connector screw.

In another presently preferred aspect, the EEG electrode is disposable. The EEG electrode base also preferably includes a housing defining a chamber for containing and dispensing an electrically conductive gel, and the housing of the EEG electrode base has a surface defining a lower gel dispenser opening for dispensing the electrically conductive gel. A porous foam pad is also preferably attached to the EEG electrode base, by insertion of an upper annular flange of the foam pad into a corresponding annular groove of the electrode base. The porous foam pad provides padding for a comfortable scalp interface, absorbs the conductive gel to maintain a consistent volume of gel between the electrode base and scalp, and compresses with minimal downward pressure to minimize slide artifacts. The foam pad is easily disposable and replaceable, and is removably mounted to the EEG electrode base by a removable bottom connector ring. The bottom connector ring is removably received in a lower annular channel of the EEG electrode base which includes a plurality of inwardly projecting tabs that are received in a corresponding plurality of slots in the bottom connector ring. An annular groove or space is formed between the bottom connector ring and the housing of the EEG electrode base, with an edge portion of the porous foam pad removably received in the annular space, so that the porous foam pad can be removed from the EEG electrode base and replaced by another porous foam pad by removing and replacing the bottom connector ring.

The EEG electrode base housing also preferably includes an upper, outer radial flange, with a plurality of slots formed in the housing and the outer radial flange, and an outer radial groove connected to each of the slots in the housing, for receiving and mating with a corresponding plurality of inner mounting tabs on the electrode locator member, respectively, for removably coupling the EEG electrode to the EEG electrode locator member.

In a presently preferred aspect, the EEG electrode includes a flexible gel fill cap having an interior plunger portion for dispensing the conductive gel from the EEG electrode gel chamber. The flexible gel fill cap includes a lower outer radial flange mounted to the upper outer radial flange of the base, and the flexible gel fill cap preferably includes an upper gel fill port, through which the electrically conductive gel may be introduced into the EEG electrode gel chamber. In another presently preferred aspect, the flexible gel fill cap is formed of a flexible, resilient material, so that by inversion of the gel cap by application of downward pressure on the gel cap to exert a pump action, the gel cap dispenses the conductive gel from the EEG electrode gel chamber. In another aspect, the EEG electrode includes an upper cap allowing the EEG electrode to be gripped for seating of the EEG electrode in the EEG electrode locator member, and in a presently preferred aspect, the upper cap has a surface defining opposing outer indentations for gripping and turning the upper cap for seating of the EEG electrode in the EEG electrode locator member.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
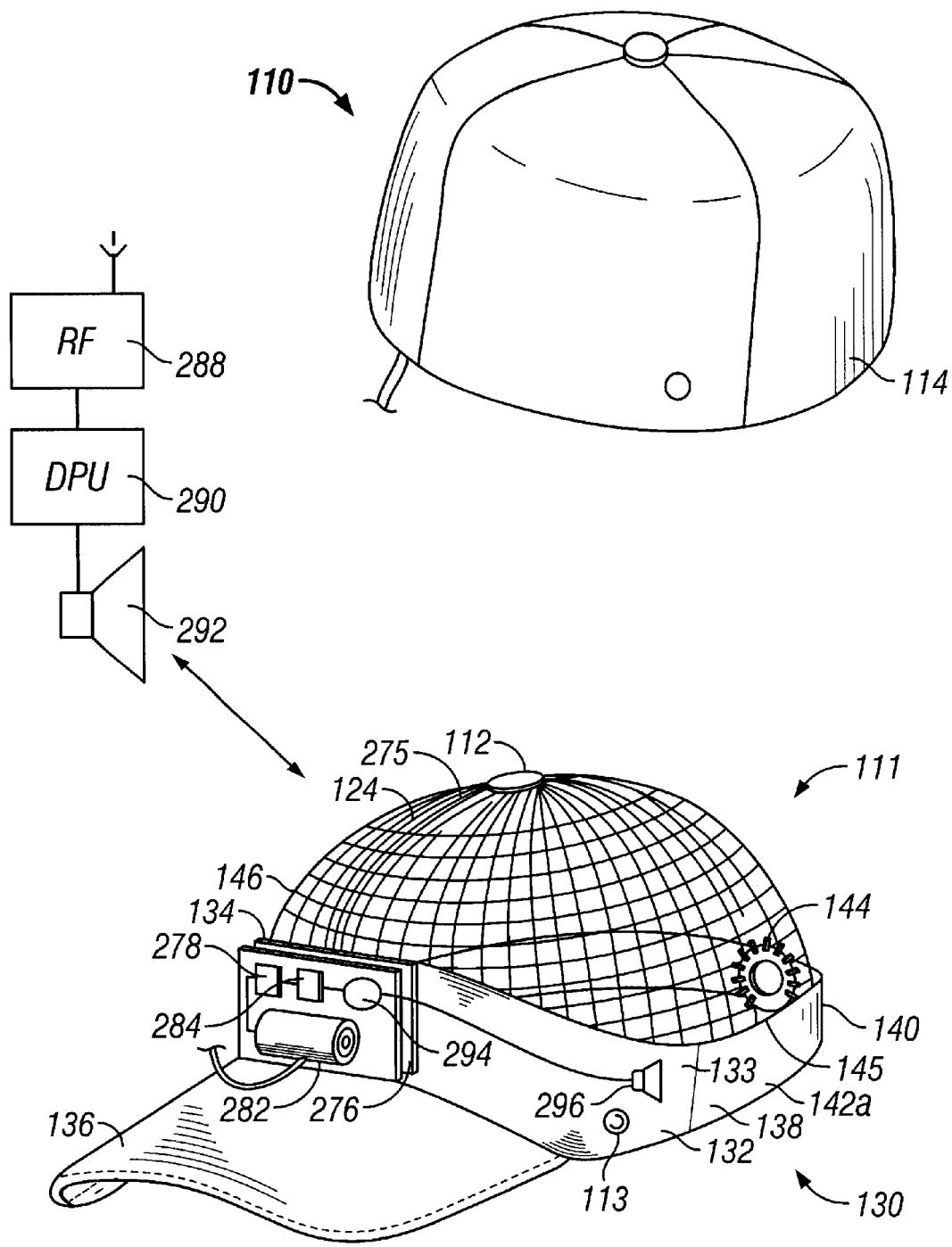
FIG. 1 is an exploded perspective view of a preferred embodiment of an EEG electrode locator headgear for use in combination with the EEG electrode and EEG electrode assembly of the present invention.

The application of EEG monitoring to common daily environments for study and monitoring of brain performance during the normal course of daily activities has been severely hampered by cumbersome detection and recording equipment, and the need for the assistance of a technician to set up and monitor the acquisition of data in order to obtain high quality data. Simply parting the hair of the scalp and preparation of the desired portions of the scalp of a subject for proper placement of electrodes has commonly required the assistance of a technician. Particularly when disposable electrodes are to be applied by a user that are not bonded to the scalp of the user to provide an electrode-scalp interface, the proper preparation and placement of an electrode over hair can be critical for obtaining high quality signal data.

As is illustrated in the drawings, the invention is embodied in an electroencephalograph (EEG) electrode locator headgear that is portable and comfortable, and allows a user to locate and apply disposable EEG electrodes accurately according to the International 10/20 System without technical assistance, to allow the acquisition of high quality EEG signals.

Figure 2:
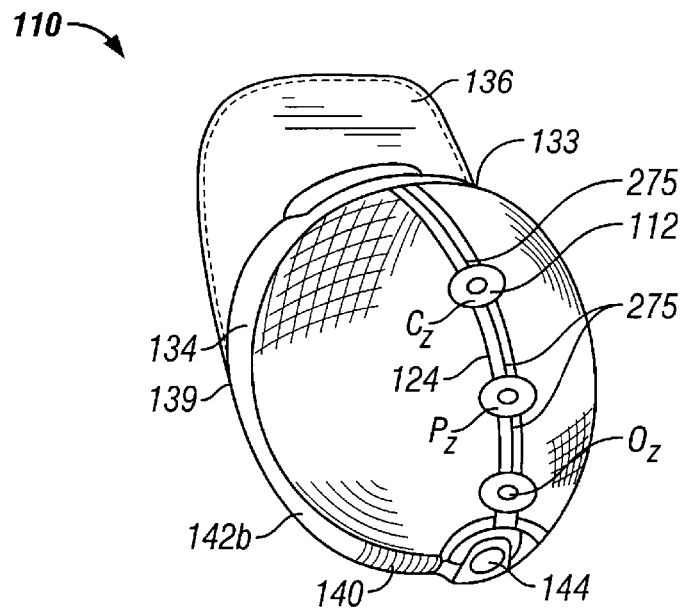
FIG. 2 is a top perspective view of the EEG electrode locator headgear of FIG. 1 without the cap shell to show the positions of the electrode locators.
Figure 3:
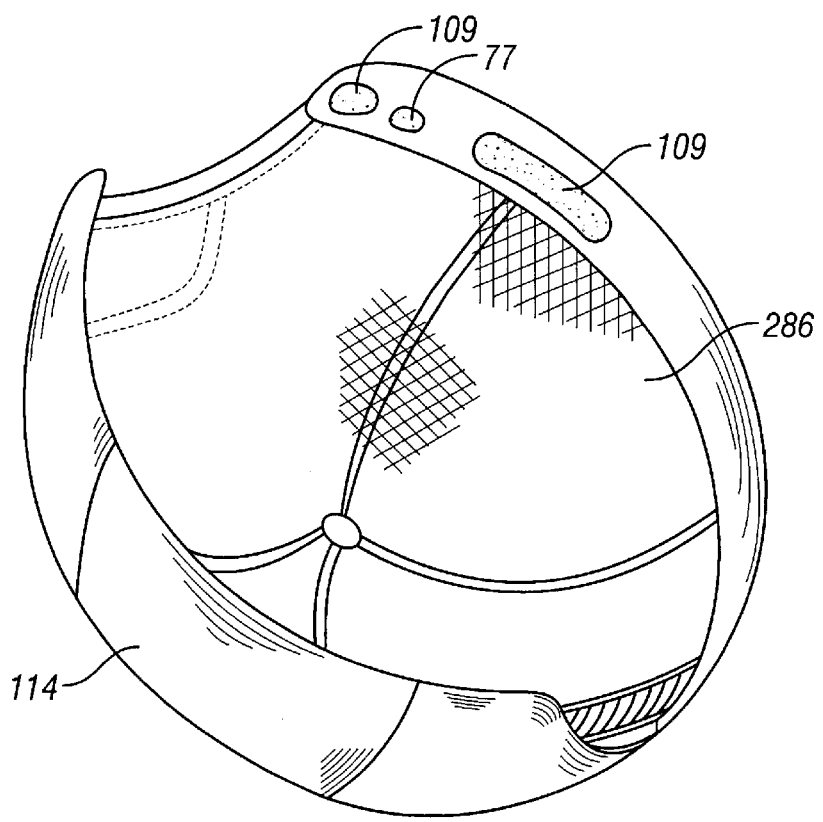
FIG. 3 is a bottom perspective view of the outer cap shell of the EEG electrode locator headgear of FIG. 2.
Figure 4:
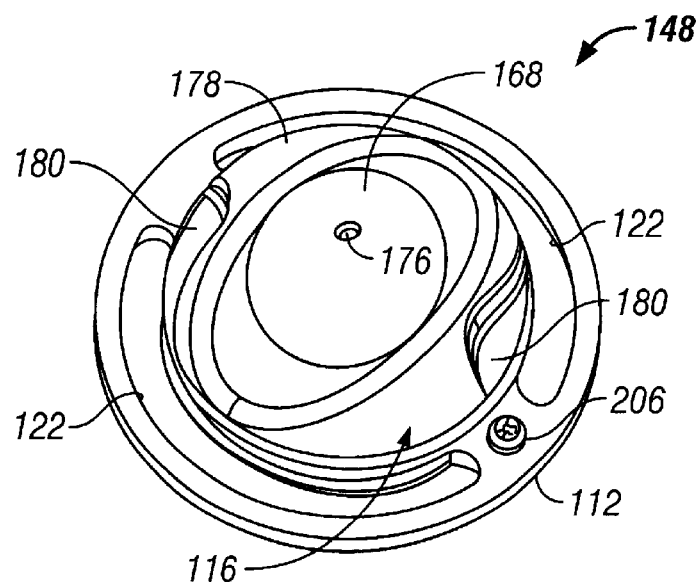
FIG. 4 is a top perspective view of the EEG electrode and the EEG electrode locator assembly of the present invention.
Figure 6:
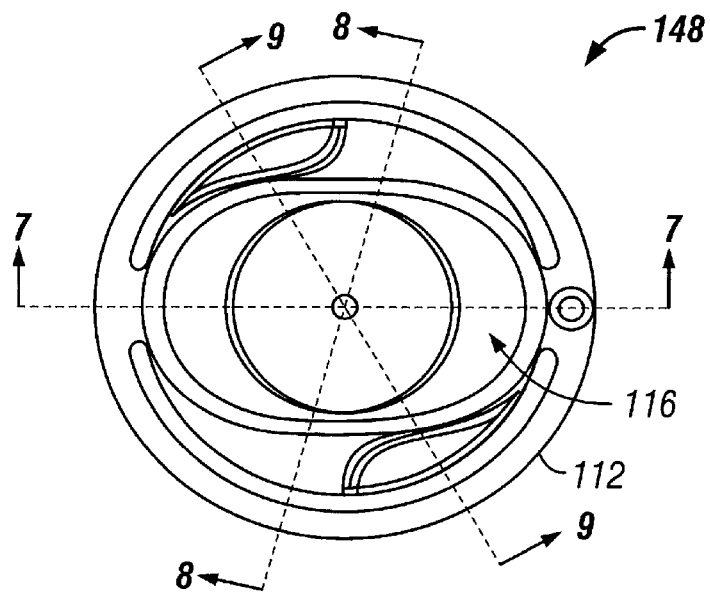
FIG. 6 is a top plan view of the EEG electrode and EEG electrode locator assembly according to the invention.
Figure 5:
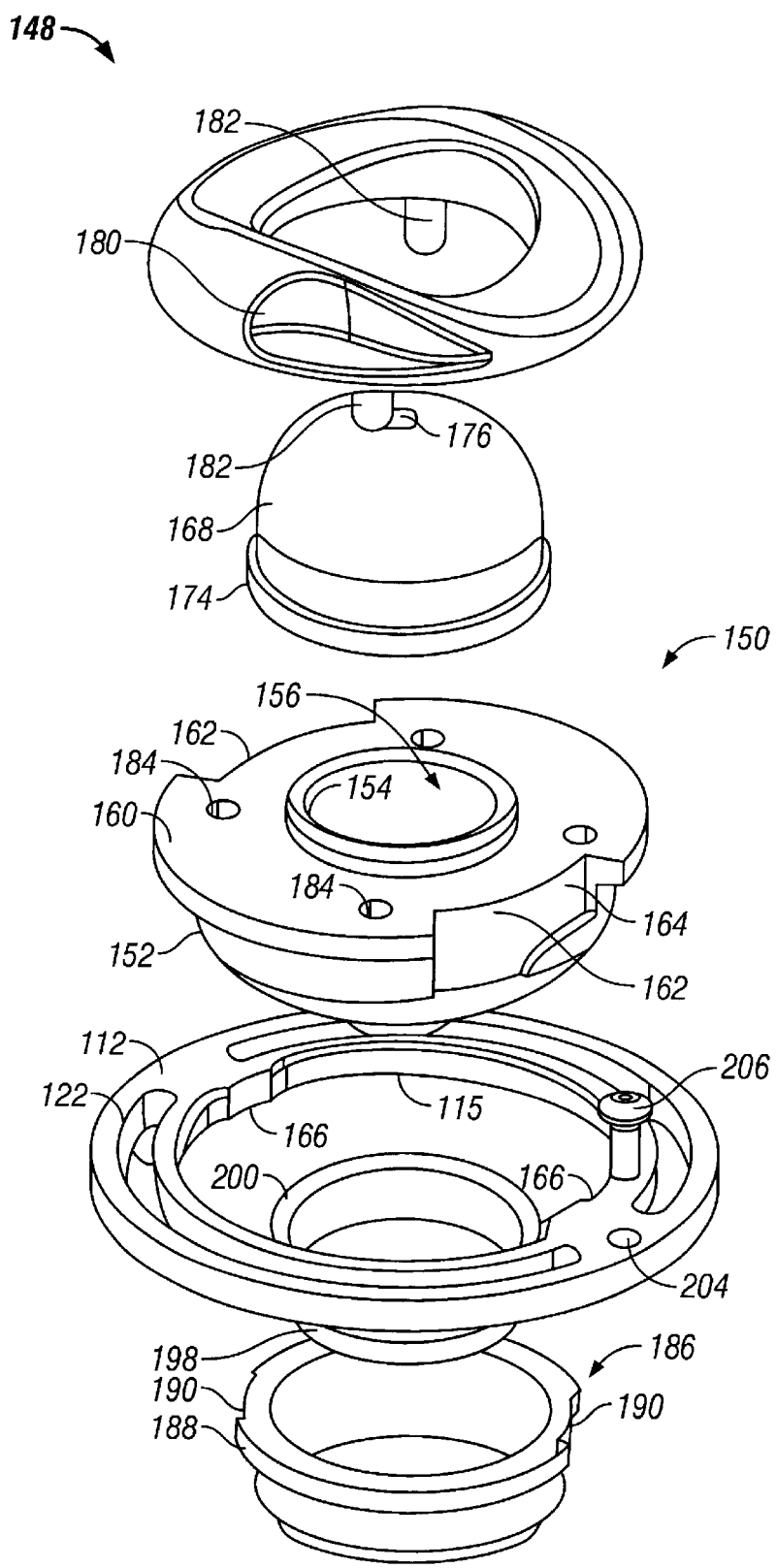
FIG. 5 is an exploded view of an EEG electrode and EEG electrode locator assembly according to the invention.

Referring to FIGS. 1 to 8, in a presently preferred embodiment, the EEG electrode and EEG electrode locator assembly of the invention are to be used in combination with an EEG electrode locator headgear such as those disclosed in U.S. Ser. No. 09/492,380 filed Jan. 27, 2000, which is hereby incorporated by reference in its entirety. The EEG electrode locator headgear 110 includes a cap portion 111 with a plurality of EEG electrode locators 112 for receiving EEG electrodes for accurate positioning on the scalp of a user. An outer cap shell 114 that can be made of cotton, wool or other fabric, for example, or the like, may be fitted over and connectable to the cap portion by one or more fasteners such as an electrically conductive connector 113, or other similar fasteners such as snaps, hook and loop fasteners 109, buttons, or the like, to protect and conceal the EEG electrode locators. The outer cap shell may also include electromagnetic shielding. The electrode locators each have a central opening 115 adapted to receive an EEG electrode 116, as is illustrated in FIGS. 4 to 9, as is further explained below. As is shown in FIGS. 4 and 5, the EEG electrode locators each are preferably slotted rings that include a plurality of slots 122 for receiving locator straps 124 that are currently preferably formed of elasticized fabric, in order to assist in biasing the electrode locators toward the scalp of the user, but non-elastic straps, such as fabric or nylon, for example, may also be suitable. Although a single locator strap or series of locator straps arranged in a line from the front to the back of the headgear may be provided, as is illustrated in FIG. 2, for locating each of the EEG electrode locators, additional locator straps may also be attached to the EEG electrode locators.

The EEG electrodes are preferably adapted to be connected for electrical communication by radio frequency (RF) transmission with an EEG monitor, which is preferably a portable EEG monitor for ambulatory use, such as the portable EEG monitor disclosed in provisional application No. 60/114,528, filed Dec. 31, 1998, and non-provisional application Ser. No. 09/345,046 filed Jun. 30, 1999, which are incorporated herein by reference in their entirety. Three EEG electrode locators are preferably provided that are adapted to be positioned at the top central (Cz), parietal (Pz), and occipital (Oz) positions relative to the scalp of a user, although alternatively additional or fewer electrode locators may also be provided in the headgear for locating EEG electrodes according to the International 10/20 system.

Referring to FIGS. 1 to 3, the base strap assembly 130 of the EEG electrode locator headgear may include a front pad of material 132, having first and second ends 133, 134, adapted to extend across a user's forehead to provide a secure footing and electrical ground for the EEG electrode locator headgear on the user's forehead. The front pad of material may be made of a non-elastic electrically conductive fabric material. A front visor or bill 136 may also be attached to the front pad of material. The base strap assembly has a first anterior end 138 connected to the first end of the front pad of material, and a second anterior end 139 connected to the second end of the front pad of material, and a posterior end 140. Together, the front pad of material and the base strap assembly are adapted to be secured comfortably around the circumference of the user's head, and the base strap assembly is adjustable. The base strap preferably comprises a pair of adjustable elastic edge straps, with first elastic edge strap 142a connected at the first anterior end 138, and the second elastic edge strap 142b being connected at the second anterior end 139 of the front pad of material, and adjustably connected together at the posterior end 140. As is illustrated in FIGS. 1 and 2, the base strap assembly may include an occipital locator device 144 adapted to be seated on a region of the user's scalp over the user's occipital bone. The base strap assembly first and second elastic edge straps thus may be connected at one end to the front pad of material, and adjustably connected at the other end to the occipital locator device 144, which may be an annular ring having a plurality of feet 145 adapted to be positioned around and over the user's occipital bone.

As is illustrated in FIGS. 1 to 3, a stretch mesh cap 146 of elastic, fabric material may also be provided in addition to, or as an alternative to, the locator straps, connected to the front pad of material, the base strap assembly, and to the plurality of EEG electrode locators for accurately positioning the plurality of EEG electrode locators relative to the scalp of a user. The stretch mesh and locator straps are preferably made of elastic material, in order to bias the electrode locators and electrodes with a downward biasing pressure toward the user's scalp, to provide a stable electrode-scalp interface capable of producing a high signal quality.

Referring to FIGS. 4 to 8, the EEG electrodes 116 are preferably of the type that are disposable, and are adapted to be seated in the electrode locators 112 to form an EEG electrode assembly 148. The EEG electrode includes an EEG electrode base member 150 having a housing 152 with a lower wall 153 defining a lower gel fill chamber 154 for containing and dispensing an electrically conductive gel 156, which is dispensed through a lower gel dispenser opening 158 shown in FIGS. 7, 8 and 9. The EEG electrode and the electrically conductive base member typically may be made from a carbon and ABS composite plastic material with a silver/silver chloride (Ag/AgCl) coating. Other electrically conductive metals or materials, such as an electrically conductive silicone, i.e. a silicone containing carbon or other electrically conductive material, may also be suitable. The EEG electrode locator member also typically may be made from a carbon and ABS composite plastic material with a Ag/AgCl coating, although the EEG electrode locator member may alternatively be made from another similar suitable electrically conductive material, such as stainless steel, for example. The EEG electrode base member housing also includes an upper, outer radial flange 160, with a plurality of slots 162, such as a pair of opposing slots as shown, formed in the housing and the outer radial flange. Each outer slot continues as an outer radial groove 164 (one of which is not visible in the drawings) in the housing, for receiving and mating with corresponding inner mounting tabs 166 of the electrode locator ring, forming a bayonet fitting for removably coupling the EEG electrode to the EEG electrode locator ring. This type of coupling advantageously allows the EEG electrode and the EEG electrode locator ring to lock together in the same orientation whenever the EEG electrode is inserted.

Figure 7:
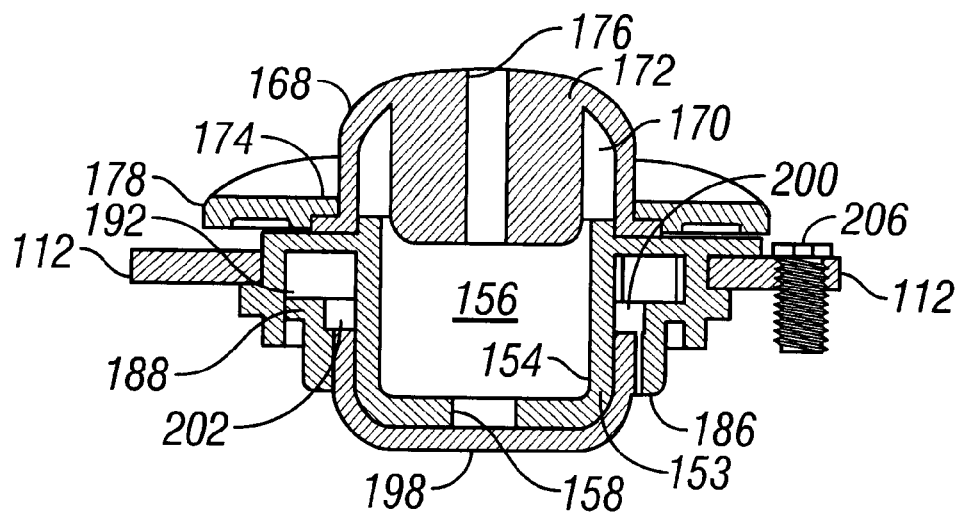
FIG. 7 is a sectional view of the EEG electrode and EEG electrode locator assembly taken along line 7—7 of FIG. 6.
Figure 8:
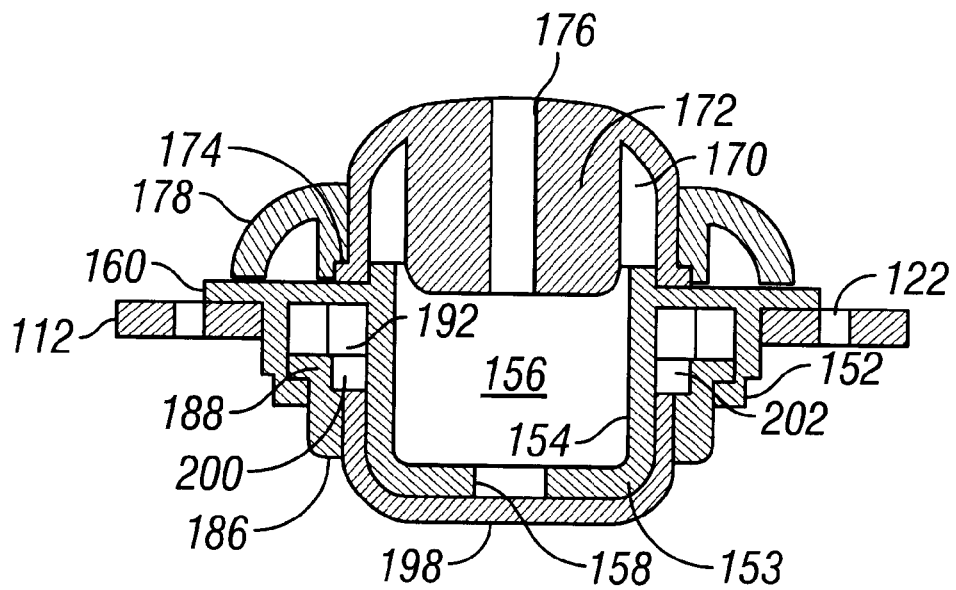
FIG. 8 is a sectional view of the EEG electrode and EEG electrode assembly taken along line 8—8 of FIG. 6.
Figure 9:
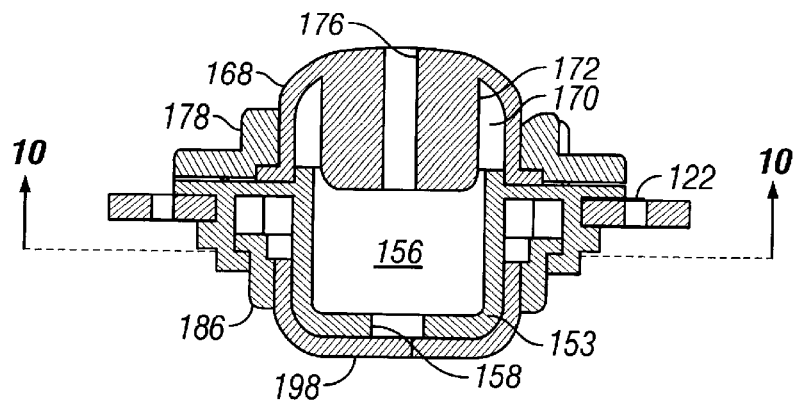
FIG. 9 is a sectional view of the EEG electrode and EEG electrode assembly taken along line 9—9 of FIG. 6.
Figure 10:
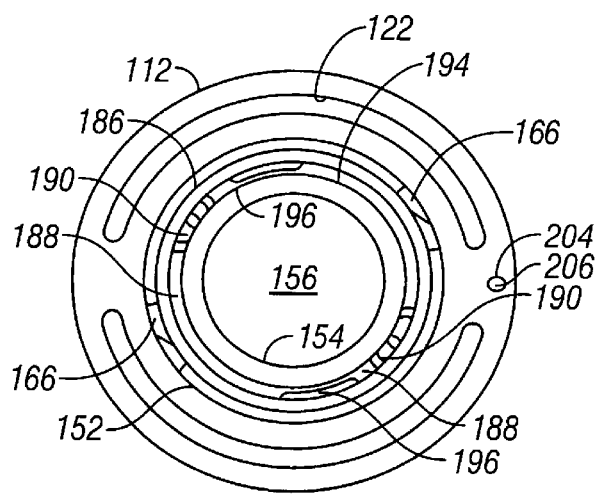
FIG. 10 is a sectional view of the EEG electrode and EEG electrode locator assembly according to the invention taken along line 10—10 of FIG. 9.
Figure 11:
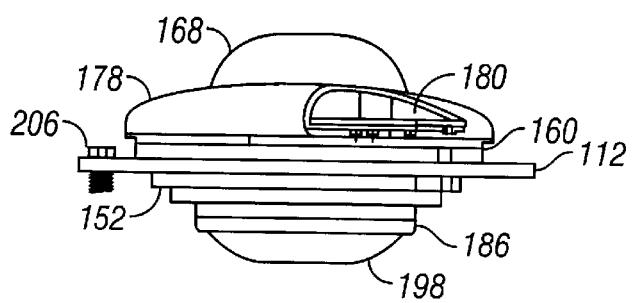
FIG. 11 is a side elevational view of the EEG electrode and EEG electrode locator assembly according to the invention.

The EEG electrode also includes a flexible gel fill cap 168 defining an upper gel chamber 170 and an interior plunger portion 172, shown in FIGS. 7, 8 and 9, for dispensing the conductive gel from the EEG electrode gel chamber as will be explained below. The flexible gel fill cap also includes a lower outer radial flange 174, and an upper gel fill port 176 through which the electrically conductive gel may be introduced into the EEG electrode gel chambers 154 and 170, such as by a syringe (not shown). The flexible gel fill cap is preferably formed of a flexible, resilient material, such as rubber, polyurethane, or other similar elastomeric materials, for example. An upper cap 178 with opposing indentations 180 allows the EEG electrode to be gripped and turned for seating of the EEG electrode in the EEG electrode locator ring. The upper cap also preferably includes a plurality of downwardly projecting posts 182, and the base member, gel fill cap, and upper cap are preferably secured together by press fitting the posts 182 into corresponding fastener apertures 184 in the base member, as illustrated in FIG. 5. Alternatively, the base member, gel fill cap and upper cap may be secured together by other types of fasteners, such as screws, bolts, or the like. The lower outer radial flange 174 of the flexible gel fill cap is captured between the upper cap 178 and the upper outer radial flange 160 of the EEG electrode base member. The upper cap and base member may alternatively, or in addition, be formed so as to snap together, securing the upper gel fill cap between them. A lower annular connector or bottom connector ring 186 is provided, having an upper radial flange 188 with a plurality of slots 190. Referring to FIGS. 5, 7, 8 and 10, the upper radial flange 188 of the bottom connector ring 186 is received in a lower annular channel 192 of the EEG electrode base member, having an interior shoulder 194 with inwardly projecting tabs 196 corresponding to and receivable in the plurality of slots 190 of the bottom connector ring, together forming a bayonet fitting of the bottom connector ring to the EEG electrode base member.

Referring to FIGS. 5, 7, 8 and 9, a porous foam pad 198, formed of a polyurethane foam, foam rubber or the like, for example, is also preferably mounted to the EEG electrode base by bottom connector ring by insertion of an outer upper annular edge or flange 200 of the foam pad into a corresponding annular groove or space 202 formed between the bottom connector ring and the lower wall of the EEG electrode base member housing. The foam pad provides padding for a comfortable scalp interface, absorbs the conductive gel to maintain a consistent volume of gel between the electrode base and scalp, and compresses with minimal downward pressure to minimize slide artifacts.

The bottom connector ring advantageously can be twisted off the EEG electrode base member, and the bottom connector ring with a new foam pad can be simply twisted back on the to EEG electrode base member. Alternatively, the foam pad can be bonded to the interior surface of the bottom connector ring, such as by adhesive, and the bottom connector ring can be disposable, so that the bottom connector ring can be twisted off and replaced by twisting a new bottom connector ring and foam pad onto the EEG electrode base member. The inside of the electrode can also be rinsed with water to wash out the remaining gel in the electrode between uses. The foam pad should be changed between uses because the salts from the electrically conductive gel will build up and increase the impedance of the EEG electrode to a point that adequate signal quality cannot be achieved. The bottom connector ring may also be made from a carbon and ABS composite plastic material with a Ag/AgCl coating, although the EEG electrode locator member may alternatively be made from another similar suitable electrically conductive material, such as stainless steel, for example. The Ag/AgCl coating improves the signal quality, but the coating may scratch off with repeated uses. Because the material from which the EEG electrode base, electrode locator member and bottom connector ring are preferably made from carbon mixed with ABS plastic, the EEG electrode with still be electrically conductive even if the Ag/AgCl coating is removed.

When the electrically conductive gel is contained in the EEG electrode gel chamber, the electrically conductive gel may be dispensed through the lower gel dispensing opening by the user by pressing on the flexible gel fill cap while covering or otherwise sealing the upper gel fill port, such as by pressing on the gel fill port with a finger, to cause inversion of the gel cap and exert a pump action, and to cause the gel cap to dispense the conductive gel from the EEG electrode gel chamber through the foam pad and through the user's hair onto the scalp of the user. Alternatively, the gel fill port may include a one-way check valve allowing filling of the gel chamber by a syringe, but not requiring any manual sealing of the gel fill port by the user to dispense the gel. The electrically conductive gel can thus be dispensed at the desired location on the user's scalp through the user's hair below the EEG electrode, to establish an effective electrical connection between the scalp of the user and the EEG electrode.

The EEG electrode locator ring also preferably includes a terminal connector aperture 204 such as for receiving a terminal connector screw 206, for connection of the electric wires 275 to the EEG electrode locator ring and the EEG electrode locator assembly. Referring to FIGS. 1 and 2, the EEG signals from the Cz, Pz, and Oz electrode locators will be routed by wires 275 from the electrode locator connector terminals via an electrical connector, which connects with electrical connector 113, as the differential inputs of the Sigma Delta analog to digital converter 276 currently preferably mounted on a circuit board at the front of the headgear, and an input is provided from a reference ground such as the front ground pad sewn into the portion of the headgear that contacts the forehead. The output of the analog to digital converter will result in a differential recording of EEG signals. The gain from the Cz electrode locator is preferably set to a gain of one, while the gains for the Pz and Oz electrode locators will be greater, and are typically 10. All filtering of the EEG signals will typically be performed digitally by programming of the analog to digital converter. The analog to digital converter, microprocessor 278, batteries 282, and an RF transmitter 284 are preferably mounted at the front of the headgear. A Faraday shield 286 is also preferably incorporated into the headgear, such as electromagnetic shielding material sewn into the outer cap shell, for example, as shown in FIG. 3, to create a Faraday shield to shield the pre-amplifiers from external noise and artifacts which may result from the use of the RF transmitter. Radio frequency transmission is currently preferred for communication of the EEG signals to an RF receiver 288 connected to a computing device 290 used for acquiring and analyzing the digital EEG signals from the user, so that no wires are required to connect the user to a recording and/or data analysis device. In one presently preferred configuration, the computing device is a data processing unit (DPU) used to acquire and analyze EEG signals from the user, and to provide feedback to the user.

The DPU preferably includes a digital signal processing (DSP) chip, power supply, digital to analog converter, a speaker 292, and batteries (not shown), so that the DPU is completely portable. The DPU can thus acquire EEG signals from the EEG electrode locator headgear, run the EEG data analysis algorithms, and use the digital to analog converter and speaker to generate audio feedback alert messages to the user. In order to provide the audio messages to the user that may be required in noisy environmental conditions, the RF transmitter 284 of the EEG electrode locator headgear and the RF receiver 288 connected to the DPU are preferably bi-directional RF transmitter-receivers, and an amplifier 294 and speaker 296 are also mounted on the EEG electrode locator headgear. Thus, when the DPU determines that an audio alert message or verbal message should be transmitted to the user, a signal is transmitted from the DPU to the EEG electrode locator headgear to present a specific message. Audio messages can be stored in analog format in flash memory in the EEG electrode locator headgear where the analog to digital converter, power supply and processor are mounted. The analog message can then be presented to the user either through one or more speakers mounted on the EEG electrode locator headgear, or through an earphone that attaches to a connector incorporated into the EEG electrode locator headgear.

It should be understood that the individual EEG electrodes can alternatively be individually or collectively directly connected such as by one or more cables to an EEG signal monitor, and that other conventional modifications may also be suitable. It should also be understood that the bayonet fitting of the EEG electrode and the EEG electrode locator ring may be reversed, so that the mounting tabs are formed in the base member of the EEG electrode, and the mounting slots and grooves receiving the mounting tabs are formed in the electrode locator ring. In addition, although the present invention contemplates the location of disposable EEG electrodes in individual EEG electrode locators, it should be appreciated that combined EEG electrode and locator assemblies, such as active, amplified electrodes, for example, may be incorporated into the headgear at the locations of the EEG electrode locators. Alternatively, active electrodes or preamplifiers could be incorporated into the EEG electrode or connected to the electrical conductor of the electrode locator. It will thus be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An electroencephalograph (EEG) electrode locator assembly for use in combination with an EEG electrode locator headgear for accurate positioning of the EEG electrode locator assembly on the scalp of a user, the EEG electrode assembly comprising:

an EEG electrode locator member adapted to be mounted to EEG electrode locator headgear;

an EEG electrode received in and removably coupled with the EEG electrode locator member, so as to be removably electrically coupled to the EEG electrode locator headgear, the EEG electrode having an electrically conductive base for electrical communication with the scalp of a user for detecting EEG signals of the user; and a porous foam pad attached to the EEG electrode base, wherein the EEG electrode base includes a housing and a surface, the housing defining a chamber for containing and dispensing an electrically conductive gel, and the surface defining a lower gel dispenser opening for dispensing the electrically conductive gel;

wherein the EEG electrode base has a surface defining a lower annular channel with an interior shoulder having a plurality of inwardly projecting tabs, and further comprising a bottom connector ring received in the lower annular channel of the EEG electrode base, the bottom connector ring having a plurality of slots corresponding to the inwardly projecting tabs of the EEG electrode base, for removably receiving and mating with the inwardly projecting tabs of the EEG electrode base, an annular groove being formed between the bottom connector ring and the housing of the EEG electrode base, an edge portion of the porous foam pad being removably received in the annular groove, whereby the porous foam pad is removably coupled to the EEG electrode base, and can be removed from the EEG electrode base and replaced by another porous foam pad by removing and replacing the bottom connector ring.

2. An electroencephalograph (EEG) electrode locator assembly for use in combination with an EEG electrode locator headgear for accurate positioning of the EEG electrode locator assembly on the scalp of a user, the EEG electrode assembly comprising:

an EEG electrode locator member adapted to be mounted to EEG electrode locator headgear; and an EEG electrode received in and removably coupled with the EEG electrode locator member, so as to be removably electrically coupled to the EEG electrode locator headgear, the EEG electrode having an electrically conductive base for electrical communication with the scalp of a user for detecting EEG signals of the user, wherein the EEG electrode base includes a housing defining a chamber for containing and dispensing an electrically conductive gel;

wherein the EEG electrode base housing includes an upper, outer radial flange, with a plurality of slots formed in the housing and the outer radial flange, and an outer radial groove connected to each of the slots in the housing, for receiving and mating with a corresponding plurality of inner mounting tabs on the electrode locator member, respectively, for removably coupling the EEG electrode to the EEG electrode locator member.

3. An electroencephalograph (EEG) electrode locator assembly for use in combination with an EEG electrode locator headgear for accurate positioning of the EEG electrode locator assembly on the scalp of a user, the EEG electrode assembly comprising:

an EEG electrode locator member adapted to be mounted to EEG electrode locator headgear; and an EEG electrode received in and removably coupled with the EEG electrode locator member, so as to be removably electrically coupled to the EEG electrode locator headgear, the EEG electrode having an electrically conductive base for electrical communication with the scalp of a user for detecting EEG signals of the user, said EEG electrode including a flexible gel fill cap, the flexible gel fill cap having a lower outer radial flange mounted to an upper outer radial flange of the EEG electrode base, wherein the EEG electrode base includes a housing defining a chamber for containing and dispensing an electrically conductive gel.

4. The EEG electrode locator assembly of claim 3, wherein the flexible gel fill cap includes an upper gel fill port, through which the electrically conductive gel may be introduced into the EEG electrode gel chamber.

5. The EEG electrode locator assembly of claim 3, wherein the flexible gel fill cap is formed of a flexible, resilient material.

6. The EEG electrode locator assembly of claim 3, wherein the flexible gel fill cap comprises an interior plunger portion for dispensing the conductive gel from the EEG electrode gel chamber.

7. An electroencephalograph (EEG) electrode for use in combination with an EEG electrode locator and an EEG electrode locator headgear for accurate positioning of the EEG electrode on the scalp of a user, the EEG electrode comprising:

an electrically conductive EEG electrode base for electrical communication with the scalp of a user for detecting EEG signals of the user, the EEG electrode receivable in and adapted to be removably coupled with the EEG electrode locator, so as to be removably electrically coupled to the EEG electrode locator headgear;

further comprising a porous foam pad attached to the EEG electrode base;

wherein the EEG electrode base includes a housing defining a chamber for containing and dispensing an electrically conductive gel; and wherein the housing of the EEG electrode base has a surface defining a lower gel dispenser opening for dispensing the electrically conductive gel;

wherein the EEG electrode base has a surface defining a lower annular channel with an interior shoulder having a plurality of inwardly projecting tabs, and further comprising a bottom connector ring received in the lower annular channel of the EEG electrode base, the bottom connector ring having a plurality of slots corresponding to the inwardly projecting tabs of the EEG electrode base, an annular groove being formed between the bottom connector ring and the housing of the EEG electrode base, an edge portion of the porous foam pad being removably received in the annular groove, whereby the porous foam pad is removably coupled to the EEG electrode base, and can be removed from the EEG electrode base and replaced by another porous foam pad by removing and replacing the bottom connector ring.

8. An electroencephalograph (EEG) electrode for use in combination with an EEG electrode locator and an EEG electrode locator headgear for accurate positioning of the EEG electrode on the scalp of a user, the EEG electrode comprising:

an electrically conductive EEG electrode base for electrical communication with the scalp of a user for detecting EEG signals of the user, the EEG electrode receivable in and adapted to be removably coupled with the EEG electrode locator, so as to be removably electrically coupled to the EEG electrode locator headgear, wherein the EEG electrode base includes a housing defining a chamber for containing and dispensing an electrically conductive gel, wherein the EEG electrode base housing includes an upper, outer radial flange, with a plurality of slots formed in the housing and the outer radial flange, and an outer radial groove connected to each of the slots in the housing, for receiving and mating with a corresponding plurality of inner mounting tabs on the electrode locator member, respectively, for removably coupling the EEG electrode to the EEG electrode locator member.

9. An electroencephalograph (EEG) electrode for use in combination with an EEG electrode locator and an EEG electrode locator headgear for accurate positioning of the EEG electrode on the scalp of a user, the EEG electrode comprising:

an electrically conductive EEG electrode base for electrical communication with the scalp of a user for detecting EEG signals of the user, the EEG electrode receivable in and adapted to be removably coupled with the EEG electrode locator, so as to be removably electrically coupled to the EEG electrode locator headgear, wherein the EEG electrode base includes a housing defining a chamber for containing and dispensing an electrically conductive gel; and a flexible gel fill cap, the flexible gel fill cap having a lower outer radial flange mounted to an upper outer radial flange of the EEG electrode base.

10. The EEG electrode of claim 9, wherein the flexible gel fill cap includes an upper gel fill port, through which the electrically conductive gel may be introduced into the EEG electrode gel chamber.

11. The EEG electrode of claim 9, wherein the flexible gel fill cap is formed of a flexible, resilient material.

12. The EEG electrode of claim 9, wherein the flexible gel fill cap comprises an interior plunger portion for dispensing the conductive gel from the EEG electrode gel chamber.

13. An electroencephalograph (EEG) electrode comprising:

a conductive base member comprising a top surface and a bottom surface, said base member forming a chamber between the top surface and the bottom surface, said chamber configured to contain an electrically conductive gel;

a porous foam pad coupled to the bottom surface of the base member; and a flexible gel fill cap coupled to the top surface of the conductive base member, said flexible gel fill cap in communication with the chamber, wherein said flexible gel fill cap is configured to receive the conductive gel.

14. The EEG electrode of claim 13 further comprising a bottom connector ring that is coupled to the conductive base member and secures the foam pad to the bottom surface of the conductive base member.

15. The EEG electrode of claim 14 further comprising an upper cap that is coupled to the top surface of the conductive base member and secures the flexible gel fill cap to the conductive base member.

16. The EEG electrode of claim 15, wherein the upper cap and the flexible gel fill cap are removably coupled to the top surface of the conductive base member.

17. The EEG electrode of claim 15, wherein the upper cap is configured for gripping and turning the cap.

18. The EEG electrode of claim 17, wherein the upper cap has a surface defining opposing outer indentations for gripping and turning the upper cap.

19. The EEG electrode of claim 14, wherein the bottom connector ring is removably coupled to the conductive base member.

20. The EEG electrode of claim 14, wherein the flexible gel fill cap comprises a flexible and resilient material capable of compression and inversion for dispensing the conductive gel through a pump action.

21. The EEG electrode of claim 13, wherein the EEG electrode is disposable.

22. The EEG electrode of claim 13, wherein the flexible gel fill cap comprises an upper gel fill port through which the electrically conductive gel may be introduced into the chamber of the conductive base member.

23. The EEG electrode of claim 13, wherein the bottom surface of the conductive base member has an opening for dispensing the conductive gel from the chamber.

24. The EEG electrode of claim 13, wherein the EEG electrode is adapted to be mounted to an EEG electrode locator.

25. The EEG electrode of claim 13, wherein the EEG electrode is removably coupled with an EEG electrode locator.

26. The EEG electrode of claim 25, wherein the electrode locator is adapted to be removably electrically coupled to an EEG headgear, the EEG electrode adapted to be in electrical communication with the scalp of a user such that EEG signals of the user are detected by the EEG electrode.

27. The EEG electrode of claim 25, wherein the EEG electrode is electrically coupled to the EEG electrode locator by a removable electrically conductive ring, said electrically conductive ring having a central opening adapted to receive the EEG electrode.

28. The EEG electrode of claim 25, wherein the EEG electrode locator has a surface defining a plurality of slots adapted for receiving at least one locator strap.

29. The EEG electrode of claim 28, further comprising a locator strap fitted through the plurality of slots.

30. The EEG electrode of claim 25, wherein the EEG electrode locator comprises means for connecting with an electrical connector.

31. The EEG electrode of claim 25, wherein the EEG electrode locator is removably coupled to an EEG headgear.

* * * * *

UNITED STATES PATENT AND TRADEMARK OFFICE
CERTIFICATE OF CORRECTION

| | | |
|---|---|---|
| PATENT NO. | : 6,640,122 B2 | Page 1 of 1 |
| APPLICATION NO. | : 09/900988 | |
| DATED | : October 28, 2003 | |
| INVENTOR(S) | : Samir Manoli et al. | |

It is certified that error appears in the above-identified patent and that said Letters Patent is hereby corrected as shown below:

Column 1, lines 12-15, delete "The United States Government has rights to this invention pursuant to research supported in the whole or in part by NIH R44-NS38036 awarded by the National Institute of Neurological Disorders and Stroke." and insert instead --This invention was made with government support under NIH contract R44-NS38036 awarded by the National Institute of Neurological Disorders and Stroke. The government has certain rights in the invention.--

Signed and Sealed this

Twenty-second Day of June, 2010

David J. Kappos
*Director of the United States Patent and Trademark Office*